US 6,589,513 B2

(12) United States Patent
Lesky et al.

(10) Patent No.: US 6,589,513 B2
(45) Date of Patent: Jul. 8, 2003

(54) ORAL HYGIENE FORMULATION AND METHOD OF USE

(75) Inventors: Joseph Lesky, Cranford, NJ (US); James Lesky, Vernon, NJ (US); Teresa Lesky, Vernon, NJ (US)

(73) Assignee: Lesko-Care, L.L.C., Cranford, NJ (US)

( * ) Notice: Subject to any disclaimer, the term of this patent is extended or adjusted under 35 U.S.C. 154(b) by 0 days.

(21) Appl. No.: 09/957,095

(22) Filed: Sep. 20, 2001

(65) Prior Publication Data

US 2002/0054858 A1 May 9, 2002

Related U.S. Application Data

(60) Provisional application No. 60/234,064, filed on Sep. 20, 2000.

(51) Int. Cl.[7] .......................... A61K 7/16; A61K 35/78; A61K 7/26
(52) U.S. Cl. .......................... 424/58; 424/49; 424/195.1
(58) Field of Search .......................... 424/195.1, 49–58

(56) References Cited

U.S. PATENT DOCUMENTS

| | | | |
|---|---|---|---|
| 5,149,521 A | 9/1992 | Hirose et al. |
| 5,376,374 A | 12/1994 | Zelaya |
| 5,472,684 A | 12/1995 | Nabi et al. |
| 5,908,613 A | 6/1999 | Bazzucco |
| 6,264,926 B1 | 7/2001 | Farooqi et al. |
| 6,350,435 B1 | 2/2002 | Alvarez Hernandez |
| 6,355,684 B1 | 3/2002 | Squires |
| 6,428,770 B1 | 8/2002 | Kayane et al. |
| 2002/0054858 A1 | 5/2002 | Lesky et al. |

*Primary Examiner*—Shep K. Rose
(74) *Attorney, Agent, or Firm*—Woodbridge & Associates, PC; Stuart H. Nissim, Esq.

(57) ABSTRACT

A formulation which promotes gum and oral health through the presence of natural components exhibiting astringent, antiseptic and local stimulant effects. The formulation can be in the form of a concentrate, an oral rinse, gel, ointment, and other topical forms. The formulation also promotes healing of sores and wounds as well as preventing toothdecay. The use of cayenne as a preferred component has a synergistic effect on other components effects.

10 Claims, No Drawings

ORAL HYGIENE FORMULATION AND METHOD OF USE

BACKGROUND OF THE INVENTION

This application claims priority from U.S. Serial No. 60/234,064 filed on Sep. 20, 2000, and its contents hereby incorporated by reference in full.

FIELD OF THE INVENTION

This invention pertains to compositions and their method of use in the maintenance and improvement of oral health, more specifically, a formulation of herbal extracts and essential oils, known by herbal health authorities to possess desired beneficial effects, which in combination provide a synergistic effect on the improvement and maintenance of gum and oral health.

DESCRIPTION OF THE ART

Gum disease and oral health problems have reached epidemic proportions. According to the American Dental Association, three out of four adults over the age of 35 have some form of gum disease. Recently, the Surgeon General issued a report on oral health.

Studies have shown that gum (periodontal) disease not only can cause the loss of teeth, but can cause much more serious diseases. Individuals with gum disease have been shown to have an increased incidence of heart disease, diabetes, and respiratory disease and have increased risk of stroke, increased buildup of plaque in carotid arteries, weakened immune systems and increased risk of complications from diabetes.

Treatment of gum disease by a periodontist usually is scaling and planning to remove hidden plaque and tartar below the gum line. In addition, in severe cases of gum disease, the diseased portions of the gums are surgically removed one quadrant at a time, and can potentially require the removal of teeth. These procedures are painful, expensive and merely treat the symptoms of the disease.

Many substances have been used individually and in combinations to improve gum and oral health. It would be highly desirable to combine the substances for optimal improvement of gum and oral health. The solution disclosed herein not only provides optimal improvement of gum and oral health, but also provides for prevention of gum and oral health problems.

SUMMARY OF THE INVENTION

A formulation is disclosed which provides optimal improvement of gum and oral health and provide for the prevention of gum and oral health problems. The invention uses a unique combination of ingredients which exhibit desired properties including antiseptic, astringent, stimulant and local analgesic properties, which in the present formulations result in the synergistic properties of all the components. The use of capsicum in the formulation has demonstrated remarkable synergistic, almost catalytic, effect with the other components of the formulation. A preferred formulation is prepared in a concentrated form. Typical use of the concentrate, uses a diluted solution of the concentrate as an oral irrigator or mouth wash which bolsters maximum penetration into gum pockets. The concentration of the solution can be varied to achieve desired results. The concentrate can also be formulated into a toothpaste, oral gel, poultice, paste, salve, and the like. In additional to helping minimize gum disease, the formulations have been shown to aid in the reduction in the formation of cavities and also promotes the healing of cold sores and wounds.

DETAILED DESCRIPTION

To achieve the desired results, the preferred formulation exhibits astringent, antiseptic (for example antibacterial, antifungal, bactericidal, and virucidal), local stimulant, anti-inflammatory, immuno-stimulant and local analgesic properties. These properties can be attained by using a combination of components, wherein each component exhibits one or more of the desired properties. The formulation can contain more than one component which exhibits the same desired property.

For ease of production, preferred components are in the form of a liquid, such as fluid extracts, tinctures, solid extracts, and the like, but can also be in the form of powders and the like. To promote health and ensure safety, it is also desirable that the components be extracts, oils, powders, etc., of naturally occurring flora and that these components are not chemically processed other than the process used to directly produce the fluid extract, tincture or oil, and are thereby suitable for use in the oral cavity.

Examples of preferred astringents include, but are not limited to, bayberry bark, white oak bark, rhatany bark, sage, and teas,.

Examples of antiseptics include, but are not limited to peppermint oil, Echinacea, bloodroot, cayenne, tea tree oil, wild bergamont, chaparral, stinging metal, bay, myrrh, rhatany bark, toothache tree, calendula, and chamomile.

Examples of local stimulants include, but are not limited to, cayenne, peppermint oil, calendula, wintergreen, bayberry, and sage.

It is contemplated that additional components may include coloring and flavoring additives. As an example of multi-property components, the use of peppermint oil takes advantage of the local stimulant and antiseptic properties as well as providing a flavoring component.

Preferred formulation s include cayenne to utilize its multiple desirable properties and its synergistic effect on the properties of other components in the formulation.

A preferred formulation is comprised of echinacea, bloodroot, bayberry, white oak bark, cayenne, tea tree oil, and peppermint oil. The echinacea provides antiseptic (antibacterial) and local analgesia as well as exhibiting some boost to the immune system. The bloodroot provides an antiseptic effect and prevents the formation of plaques from bacteria, most likely through the presents of the antiseptic sanguinarine which prevents several types of oral bacteria from forming dental plaque. The bayberry tightens gums and provides antiseptic, astringent and local stimulant effects. The white oak bark also tightens gums and provides astringent, antiseptic and anti-inflammatory effects. The cayenne acts as an antibacterial, stimulates circulation, blocks pain, and also supplies a synergistic effect on the effects of the other components in the formulation. The tea tree oil provides antiseptic (antibacterial) and anti-inflammatory effects. The peppermint oil stimulates circulation, provides antiseptic effects and acts as a flavoring agent and breath freshener.

A preferred formulation is comprised of

| | |
|---|---|
| 0–60% by volume | Echinacea |
| 0–30% by volume | Bloodroot |
| 0–30% by volume | Bayberry Bark |
| 0–30% by volume | White Oak Bark |
| 0–15% by volume | Cayenne |
| 0–10% by volume | Tea Tree Oil |
| 0–2% by volume | Peppermint Oil |

Another preferred formulation for the composition is comprised of

| | |
|---|---|
| 35.4% by volume | Echinacea |
| 17.7% by volume | Bloodroot |
| 17.7% by volume | Bayberry Bark |
| 17.7% by volume | White Oak Bark |
| 6.6% by volume | Cayenne |
| 4.4% by volume | Tea Tree Oil |
| 0.5% by volume | Peppermint Oil |

The above formulations result in a concentrate which can be used in any number of application methods, formulations and compositions. For example, the concentrate can be diluted with water and used as a mouthwash. A preferred rinse comprises up to 5% by volume of the concentrate diluted with purified water. The concentrate could be impregnated in or coated on a dental floss or fibers of a toothbrush. The concentrate can also be added to a toothpaste base, oral gel, or other oral compositions. The concentrate can also be used by placing 1–2 drops directly on a toothbrush or on commercially available toothpaste and used to brush the teeth and gums.

After application, for example by rinsing, brushing, or application of a gel, or the like, it is preferable that the mouth is not rinsed, however; rinsing after use, as for example if used in or with a toothpaste, will not dramatically reduce the effectiveness of the composition.

The concentrate can also be applied directly, or with some suitable carrier, to cold sores (chancre sores) in or around the mouth. The concentrate provides pain relief and also promotes the healing of the sore.

The concentrate can also be applied directly, or with a suitable carrier, to wounds, including lacerations, incisions, surgical incisions, etc., to provide pain relief and the promotion of healing, as well as antiseptic. The concentrate also appears to reduce the formation of scar tissue in/on such wounds.

The following examples are provided for illustrative purposes and are not presented as a limitation on the scope of this invention.

EXAMPLE 1

A concentrate was prepared by combining and mixing:

2 fluid ounces of Echinacea fluid extract (Nature's Answer);

1 fluid ounce of bloodroot (whole rhizome extract, Herb Pharm, Oregon);

1 fluid ounce of bayberry bark fluid extract (Nature's Answer);

1 fluid ounce of white oak bark fluid extract (Nature's Answer);

⅓ fluid ounce of cayenne, prepared by mixing two (2) teaspoons full of cayenne (180 Heat Unit powder, Star West Botanicals, Inc.) in enough of 60%/40%—water/ethanol to yield ⅓ of a fluid ounce;

¼ fluid ounce tea tree oil (100% pure oil, Herbal Authority); and about 25 drops of peppermint oil (100% pure USP, NOW Foods)

EXAMPLE 2

A mouth rinse was prepared by adding 1% by volume of the composition of Example 1 to 99% by volume purified water.

EXAMPLE 3

A composition was prepared by combining and mixing:

35.4% by volume of Echinacea fluid extract (Nature's Answer);

17.7% by volume of bloodroot (whole rhizome extract, Herb Pharm, Oregon);

17.7% by volume of bayberry bark fluid extract (Nature's Answer);

17.7% by volume of white oak bark fluid extract (Nature's Answer);

6.6% by volume of cayenne, prepared by mixing equal parts of cayenne (180 Heat Unit powder, Star West Botanicals, Inc.) with 60%/40%—water/ethanol;

4.4% by volume tea tree oil (100% pure oil, Herbal Authority); and 0.5% by volume of peppermint oil (100% pure USP, NOW Foods)

EXAMPLE 4

The concentrate of Example 1 was prepared wherein the cayenne was in the form of a solid extract (Gaia Herbs, 1,050,000 HU powder) in an amount to obtain the equivalent "heat" of the 180 HU powder.

EXAMPLE 5

A toothpaste is prepared by mixing a sufficient amount of the composition with a toothpaste base or a commercially available toothpaste, to provide about one (1) drop of the composition per each measured use of toothpaste.

EXAMPLE 6

An oral gel is prepared by mixing a sufficient amount of the composition with a suitable oral gel, (for example Orabase® by Colgate), to provide about one (1) drop of the composition per each measured use of oral gel.

EXAMPLE 7

A topical ointment is prepared by mixing 1–25 drops of concentrate in 28 grams (1 ounce) of petrolatum.

EXAMPLE 8

A topical salve was prepared by mixing concentrate, dropwise, with 28 grams (1 ounce) of cayenne powder (180 Heat Unit powder, Star West Botanicals, Inc.) until the desired paste consistency was obtained.

EXAMPLE 9

A person having periodontal pockets in excess of 12 mm (almost ½ inch) deep had been recommended for treatment by surgery. In lieu of surgery the person began orally rinsing, twice-a-day, with the oral rinse from Example 2. After two months of rinsing the periodontal pockets were reduced to about 7 mm. After another two months of rinsing the periodontal pockets were reduced to about 5 mm. After another two months of rinsing the periodontal pockets were reduced to an average of about 3–4 mm. Treatment also included cleaning every three months as well as daily brushing and flossing. After the six months of rinsing, no surgery was necessary.

EXAMPLE 10

A person having periodontal pockets in excess of 6–7 mm deep had been recommended for extensive scaling and planing of the teeth. In lieu of scaling and planing the person began rinsing daily with the oral rinse from example 2. After 3 months of rinsing the periodontal pockets were reduced to a point where no scaling or planing was needed.

EXAMPLE 11

A person having a laceration was treated with 10 surgical stitches. After 10 days the stitches were removed and the wound partially reopened. After an additional week of daily applications of a triple antibiotic, the wound showed limited healing, including the presence of a visible break (a "hole") in the skin. The topical salve of Example 8 was applied to the wound and the wound was covered and bandaged. The topical salve and bandage were reapplied daily for about 1 week after which the wound was completely closed—the "hole" had disappeared with minimal scaring.

EXAMPLE 12

A person rinsing daily with the oral rinse of Example 2 for a period of 4 years showed no signs of developing carries (cavities).

What is claimed is:

1. A cayenne synergized oral hygiene formulation consisting essentially of 35.4%–60% by volume Echinacea fluid extract, 17.7%–30% by volume bloodroot whole rhizome extract, 17.7–30% by volume bayberry bark fluid extract, 17.7%–30% by volume white oak bark fluid extract, 6.6%–15% by volume cayenne powder, 4.4%–10% by volume tea tree oil, and 0.5%–2% by volume peppermint oil, said formulation being a member of the group consisting of mouthwash, toothpaste, oral gel, ointment, salve, floss, toothbrush bristle, and dental formulation.

2. A dental formulation comprising 0–5% by volume of the composition of claim 1 with the remainder being purified water.

3. The formulation of claim 1, which comprises a mouthwash.

4. The formulation of claim 1, which comprises a toothpaste.

5. The formulation of claim 1, which comprises a floss.

6. The formulation of claim 1, which comprises a toothbrush bristle.

7. The formulation of claim 1, which comprises topically applied ointment or salve.

8. A method of enhancing dental health by topically administering the formulation of claim 1.

9. A method of treating or preventing gum diseases and tooth decay by topically administering the formulation of claim 1.

10. A method of promoting the healing of wounds by topically administering the formulation of claim 1.

* * * * *